United States Patent
Ljungström et al.

(10) Patent No.: US 6,571,130 B1
(45) Date of Patent: May 27, 2003

(54) MEDICAL IMPLANT WITH PIEZOELECTRIC MATERIAL IN CONTACT WITH BODY TISSUE

(75) Inventors: Karin Ljungström, Hässelby (SE); Kenth Nilsson, Åkersberga (SE); Johan Lidman, Stockholm (SE); Charlotte Kjellman, Stockholm (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/673,747

(22) PCT Filed: Apr. 21, 1999

(86) PCT No.: PCT/SE99/00645

§ 371 (c)(1),
(2), (4) Date: Oct. 20, 2000

(87) PCT Pub. No.: WO99/53972

PCT Pub. Date: Oct. 28, 1999

(30) Foreign Application Priority Data

Apr. 22, 1998 (SE) ............................................. 9801405

(51) Int. Cl.⁷ ................................................ A61N 1/05
(52) U.S. Cl. ........................ 607/116; 600/374; 607/122
(58) Field of Search ............................ 607/36, 116–122; 600/373–381

(56) References Cited

U.S. PATENT DOCUMENTS

| 2,976,246 A | | 3/1961 | Egerton et al. |
|---|---|---|---|
| 4,675,123 A | * | 6/1987 | Tsunooka et al. ...... 252/62.9 R |
| 4,698,318 A | | 10/1987 | Vogel et al. |
| 4,895,574 A | * | 1/1990 | Rosenberg .................... 623/24 |
| 4,917,810 A | * | 4/1990 | Tsunooka et al. ...... 252/62.9 R |
| 4,947,854 A | | 8/1990 | Rabinowitz et al. |
| 5,169,551 A | * | 12/1992 | Tsunooka et al. ...... 252/62.9 R |
| 5,684,061 A | | 11/1997 | Ohnishi et al. |

FOREIGN PATENT DOCUMENTS

| EP | 0 542 514 | 5/1993 |
|---|---|---|
| EP | 0 824 935 | 2/1998 |
| WO | WO 95/19796 | 7/1995 |

OTHER PUBLICATIONS

"Metastable Ferroelectric Sodium Niobate," Dungan et al., J. Amer. Ceram. Soc., vol. 47 (1964), pp. 73–76.
"Polarization of $NaNbO_3$–$KNbO_3$ Ceramic Solid Solutions," Dungan et al., J. Amer. Ceram. Soc., vol. 48 (1965) p. 601.
"Conventionally Sintered ($Na_{0.5},K_{0.5}$) $NbO_3$ with Barium Additions," Ahn et al., J. Amer. Ceram. Soc., vol. 70 (1987) pp. C–18–C–21.
"(K,Na)$NbO_3$ Ferroelectric Films Synthesized by Cathode Sputtering," Margolin et al., Sov. Phys. Tech. Phys., vol. 33, No. 12 (1988), pp. 1435–1438.
"Ferroelectric Potassium Sodium Niobate (K,Na) $NbO_3$ Thin Films Deposited by rf Cathode Sputtering," Margolin et al., J. Tech. Phys. (Aug. 1987).
"Ferroelectric Properties of (K,Na)$NbO_3$, Thick–Films Prepared by Rapid–Quenching," Takahashi et al. Ferroelectrics, vol. 95 (1989) pp. 209–213.

(List continued on next page.)

Primary Examiner—Jeffrey R. Jastrzab
(74) Attorney, Agent, or Firm—Schiff Hardin & Waite

(57) ABSTRACT

A medical implant has an element with at least a part thereof which is composed of piezoelectric material. The piezoelectric material is suitable for contact with body tissue and/or body fluids, and has the formula $Na_xK_yNbO_3$, with $0 \leq x \leq 0.8$, $0.2 \leq y \leq 1$, and $x+y=1$.

14 Claims, 6 Drawing Sheets

OTHER PUBLICATIONS

"Bone Bonding Ability of An Apatite–Coated Polymer Produced Using a Biomimetic Method: A Mechanical and Histological Study in vivo," Nagano et al., J. of Biomed. Matls. Res., vol. 31, No. 4, pp. 487–494 (Internet Abstract).

"Self–setting Bioactive and Biodegradable TTCP–DCPD Apatite Cement," Hamanishi et al., J. Biomed. Matls. Res., vol. 32, No. 3, pp. 383–389 (Internet Abstract).

Piezoelectric Properties of Single Crystal Berlinite, Ozimek et al. 1979 IEEE Int. Frequency Control Symposium, Index 1–33–80 (Internet Abstract).

"The Elastic Dielectric and Piezoelectric Constants of Berlinite," Bailey et al., 1982 IEEE Int. Frequency Control Symposium, Index 1–36–124 (Internet Abstract).

"Isostatically Hot–Pressed Sodium–Potassium Niobate Transducer Material for Ultrasonic Devices," Egerton et al. Amer. Ceram. Soc. Bulletin, vol. 47 (1968) pp. 1151–1156.

"Piezoelectric and Dielectric Properties of Ceramics in the System Potassium–Sodium Niobate," Egerton et al., J. Amer. Ceram. Soc., vol. 42 (1959), pp. 438–442.

"Hot Pressing of Potassium–Sodium Niobates," Jaeger et al., J. Amer. Ceram. Soc., vol. 45 (1962), pp. 207–213.

* cited by examiner

Exp 1

Exp 2

Exp 1

Exp 2

FIG. 5E
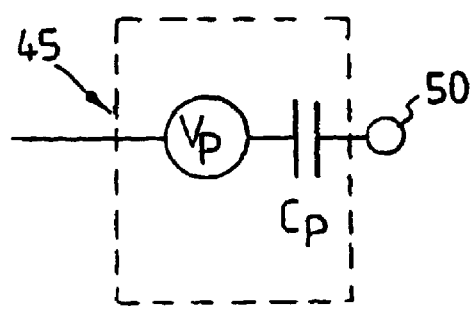
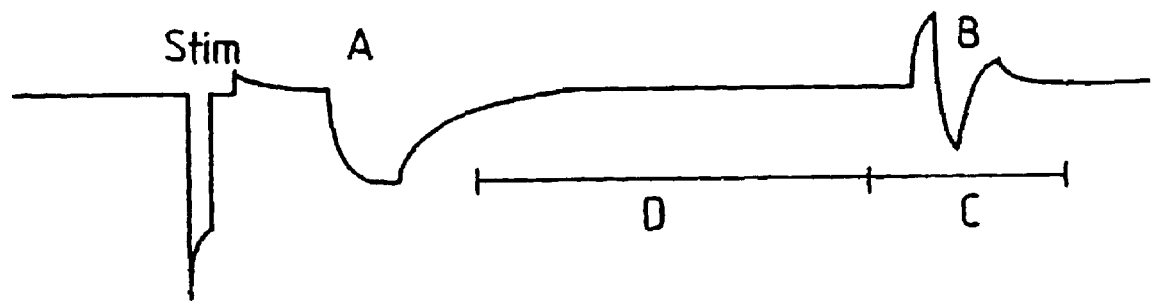
FIG. 6

MEDICAL IMPLANT WITH PIEZOELECTRIC MATERIAL IN CONTACT WITH BODY TISSUE

BACKGROUND OF THE INVENTION

1. Field of the Invention

The present invention is directed to a medical implant having at least a part thereof which comes into contact with body tissue and/or body fluids.

2. Description of the Prior Art

Piezoelectric materials have a widespread use in the medical field. The materials have for instance found use in electrodes and sensors for implantation in the body of a living being.

The sensors may for instance be accelerometers measuring the general movements of the body or the movements of the heart or parts thereof. The sensors may also be pressure sensors or sensors based on emitting/receiving ultrasound. The electrodes may be electrodes for mechanical/electric stimulation.

The piezoelectric materials used in the medical field for sensing purposes or for mechanical stimulation must meet high standards in regard of for instance sensitivity and durability. One consequence of this is that many known piezoelectric materials are less suitable for this purpose.

The commercially available biocompatible sensor materials have the disadvantage that sensors made of these materials consume too much current. Their mechanical and chemical strength is poor and is not sufficient for a lifetime of for instance 10 years. The biological stability also is poor since clotting and overgrowth reduces the efficiency of the sensors in view of their inherent softness. In spite of blood attenuating additives in the sensitive membrane, the best commercial sensors have a maximum lifetime of only six months.

Biocompatible phosphate glass ceramics that may contain crystal phases of apatite and $AlPO_4$ in the tridymite and/or berlinite form are disclosed in U.S. Pat. No. 4,698,318. Berlinite is an isotype to quartz and has inherent piezoelectric properties. It is suggested that the piezoelectric properties of berlinite can be utilized to promote healing of bone fractures. Berlinite has relatively weak piezoelectric properties. Since the berlinite forms only a part of the material, the overall piezoelectric properties of this material are weak. The piezoelectric properties are obtained by thermal treatments at relatively high temperatures for long time periods, said to cause targeted precipitation of apatite or of apatite and $AlPO_4$-crystals. The long-term stability of the material in the implanted state is not discussed, but hydroxylapatite and apatite are at least to some extent biodegradable.

The piezoelectric materials meeting the desirable, high standards that are necessary or desirable for implants normally contain components that pose a risk of being harmful in the implanted state, for instance lead, as for instance in lead titanate, lead metaniobate or lead zirconate, and it thus is undesirable that these materials directly or indirectly come into contact with body tissue or fluids. To eliminate such risks, however small, it is advisable to carefully enclose the piezoelectric material in an inert, stable enclosure meeting very high standards as to longevity. For instance, sensors normally are left in the body for a very long time and often are not removed at all, even in the event of failure. One example of this is pacer electrodes/sensors for implantation in the heart.

Apart from complicating the design of the implants as well as increasing the cost thereof, the enclosures may also adversely affect the sensitivity of the piezo structure, since the mechanical forces involved in the function of the piezo material must be transferred through at least one wall of the enclosure.

SUMMARY OF THE INVENTION

An object of the invention is to provide a piezoelectric medical implant that has a sensitivity and a durability that meets the high standards required and which further is biocompatible, i.e. which may be allowed to come into contact with body tissue or fluids.

The above object is achieved in accordance with the present invention in a medical implant having an element with at least a part thereof composed of piezoelectric material, the piezoelectric material comprising $Na_xK_yNbO_3$, with $0 \leq x \leq 0.8$, $0.2 \leq y \leq 1$, and $x+y=1$.

It has surprisingly been found that the above-described piezomaterials have a biocompatibility comparable to that of titanium.

DESCRIPTION OF THE DRAWINGS

FIG. 5E shows the equivalent circuit for the piezoelectric electrode in accordance with the invention.

FIG. 6 is a pulse diagram for the detector input signal generated by the electrodes shown in FIGS. 5A through 5E.

DESCRIPTION OF THE PREFERRED EMBODIMENTS

Figure 1A:
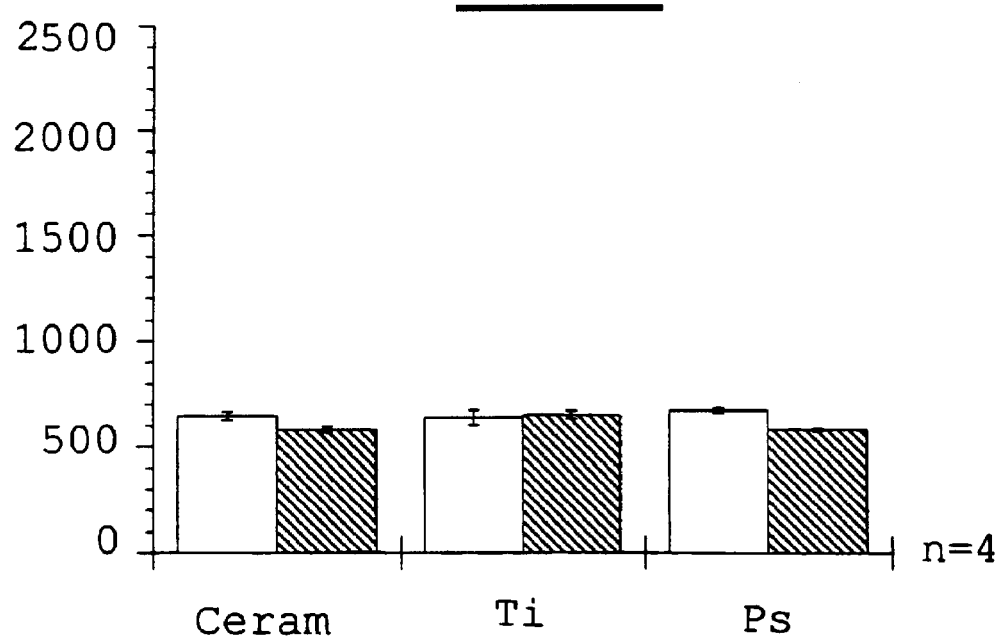
FIGS. 1A and 1B illustrate the biocompatibility of the material of the invention by means of the lactate dehydrogenase (LDH) activity in B—B units/ml in a culture medium after 23 hours and 46 hours cultivation of $1 \times 10^6$ human monocytes, on a ceramic surface (Ceram), on a titanium surface (Ti), and on tissue culture polystyrene (ps), for two different donors, respectively.

In a preferred embodiment of the invention, the piezo material consists of $Na_{0.5}K_{0.5}NbO_3$. This material surprisingly has been found to have excellent properties for the use in implantable sensors. The material thus combines the following properties:

a very high level of biocompatibility, mechanical and chemical stability expected to be at least ten years, a $d_{33}$ that can exceed 100 pCN$^{-1}$,
resistivity that can exceed $10^{12}$ Ωm,
Curie temperature >160° C., Additionally, the material will function as desired at a working temperature of 36–41° C.,
a band width of 0.3–20 Hz.

These properties obviously are well suited for use in the human body and particularly for use in pacers. When the material is used in a sensor in direct contact with tissue, the hardness of the material also has the consequence that clotting and overgrowth will not impair the sensor properties to any large extent.

The material has been used in ultrasonic applications and it consequently should be usable also for medical ultrasonic applications.

It should be noted that it is possible to provide the material according to the invention with piezoelectrical properties that are better than the corresponding properties of berlinite by a factor of 100.

The piezo material preferably should have a maximum pore size of 4 μm and a maximum grain size of 4 μm.

The relative density of the piezo material preferably should exceed 97% in order to obtain the best piezoelectric properties. In some applications, other properties might more be desirable than the best piezoelectric properties. One example is for instance an electrode for endocardial stimulation/sensing. In this application it may be more desirable to optimize the active surface (e.g. have a highly porous surface) than to optimize the piezoelectric properties.

The material may be made as a bulk material by means of the hot isostatic pressing methods using sodium carbonate, potassium carbonate and niobium pentoxide as precursors as defined in the following articles from American Ceramic Society Bulletin by Egerton—Dillon in 42(1959) pp438–442, by Jaeger—Egerton in 45(1962) pp209–213 and by Egerton—Bieling in 47(1968) pp1151–1156.

The material also may be made in the form of films or layers on substrates by means of cathode-sputtering methods as for instance described in Margolin et al, "(K,Na)NbO$_3$ ferroelectric films synthesized by cathode sputtering", Sov. Phys. Tech. Phys. 33(12), December 1988, or by other suitable thin film techniques.

The excellent biocompatible properties of the material is illustrated by the following standard toxicology test.

In this test monocytes were cultured on the surface of (Na,K)NbO$_3$, (ceram) and on two control surfaces titanium (Ti) and Polystyrene (Ps). The cytoplasmic enzyme lactate dehydrogenase (LDH) is detected extracellularly and is an indicator of the degree of injury inflicted to cells. Measurements of LDH were performed on the cellular medium after 23 h and after 46 h.

Cells can be activated and deteriorated not only by direct material interactions but also by soluble factors, including chemicals released from the material, so therefore the study also examined if there were any bacterial products (endotoxin) present in the culture medium before and after the test.

The result show that human monocytes in terms of viability are not negatively affected during culture up to 46 hours by the presence of (Na,K)NbO$_3$.

Figure 1B:
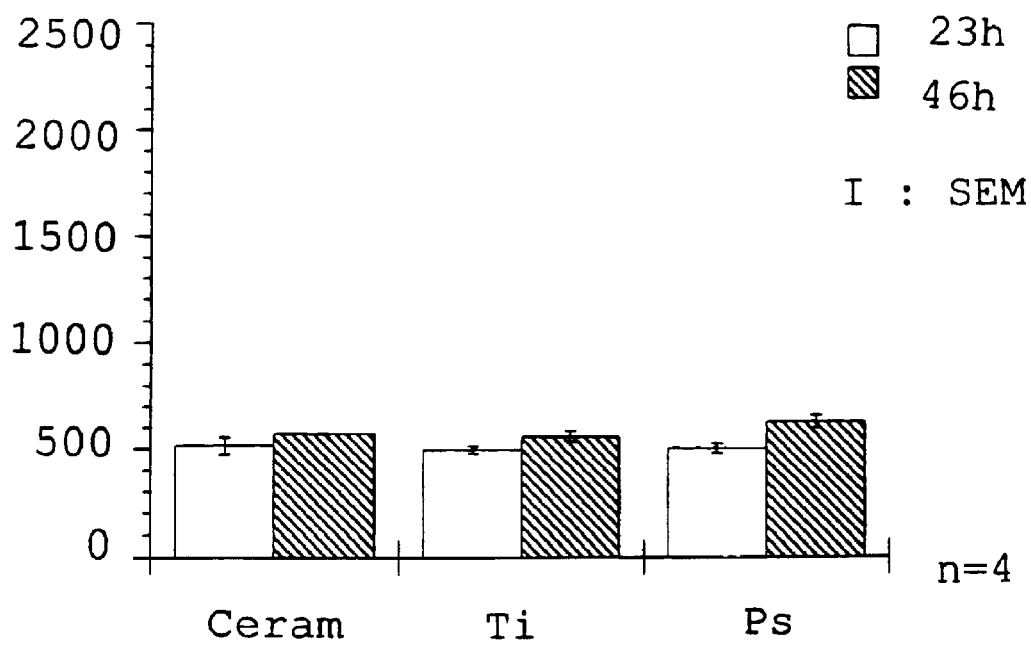
Figure 2A:
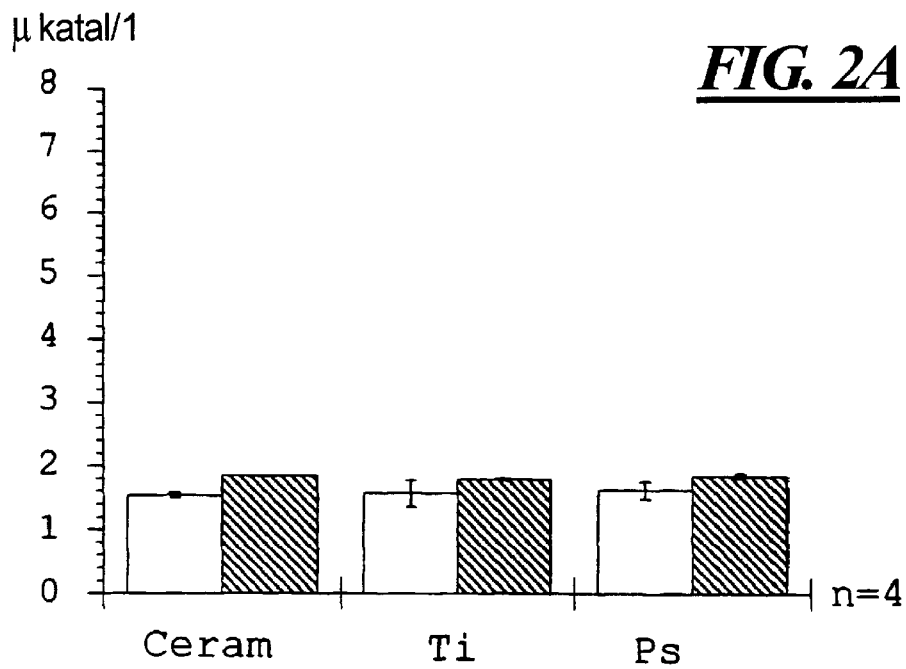
FIGS. 2A and 2B show the LDH activity as $\mu$katal/l in the culture medium after 23 hours and 46 hours cultivation of $1 \times 10^6$ human monocytes on the same surfaces as in FIG. 1, for two different donors, respectively.
Figure 2B:
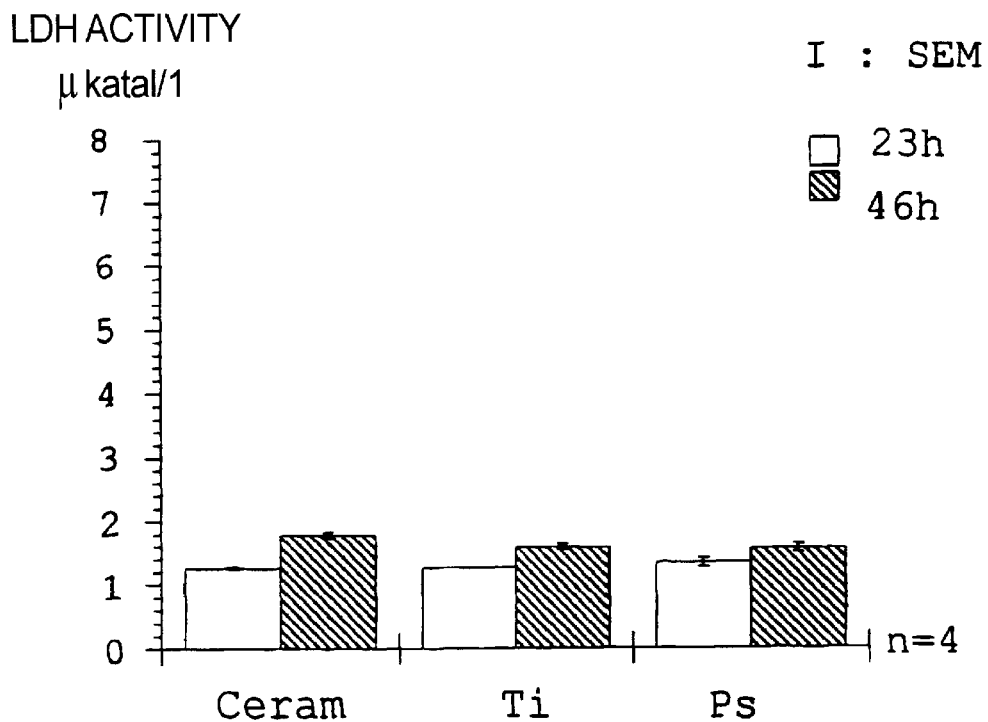
Figure 3A:
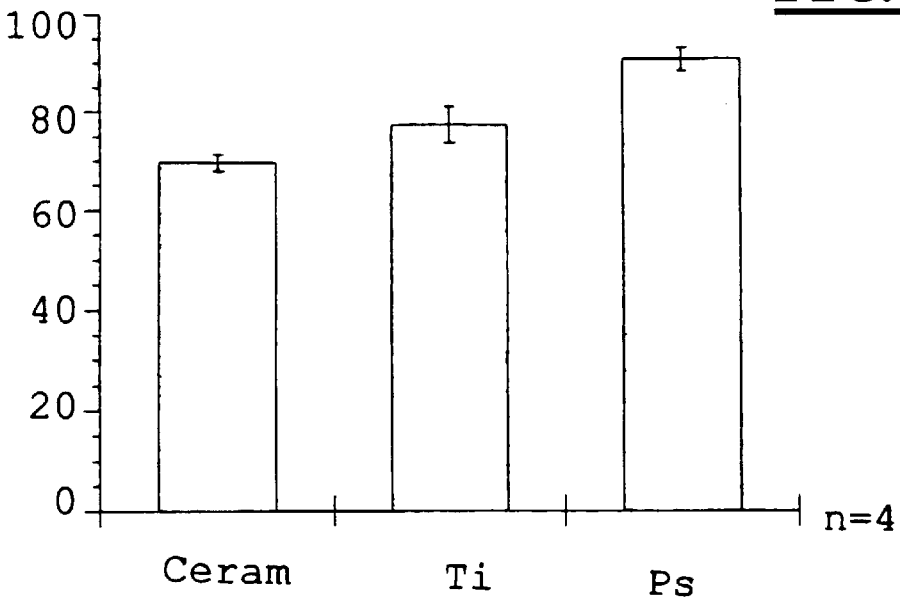
FIGS. 3A and 3B show the LDH activity in B—B units/ml, normalized by a total amount of DNA in wells after 46 hours cultivation of $1 \times 10^6$ monocytes on the same surfaces as in FIG. 1, for two different donors, respectively.
Figure 3B:
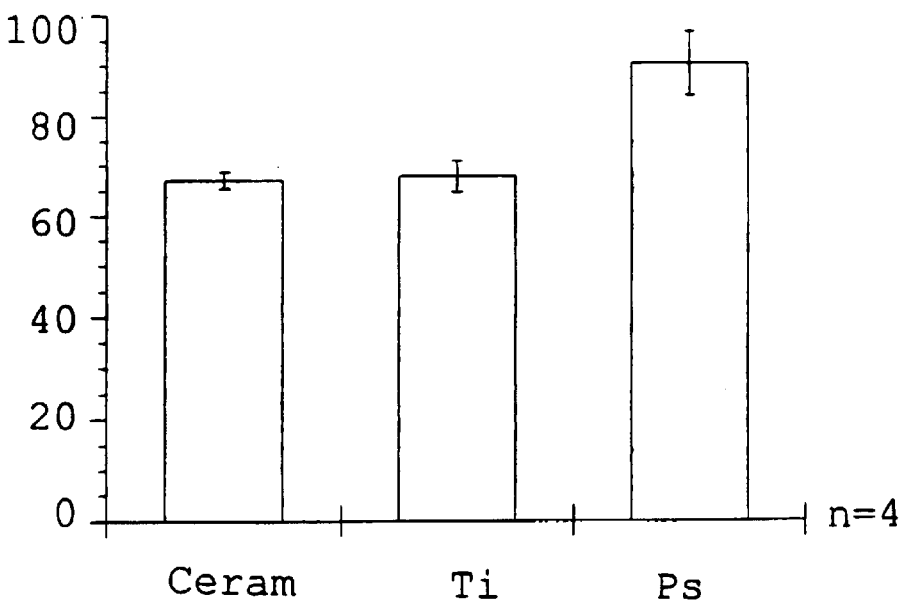
Figure 4:
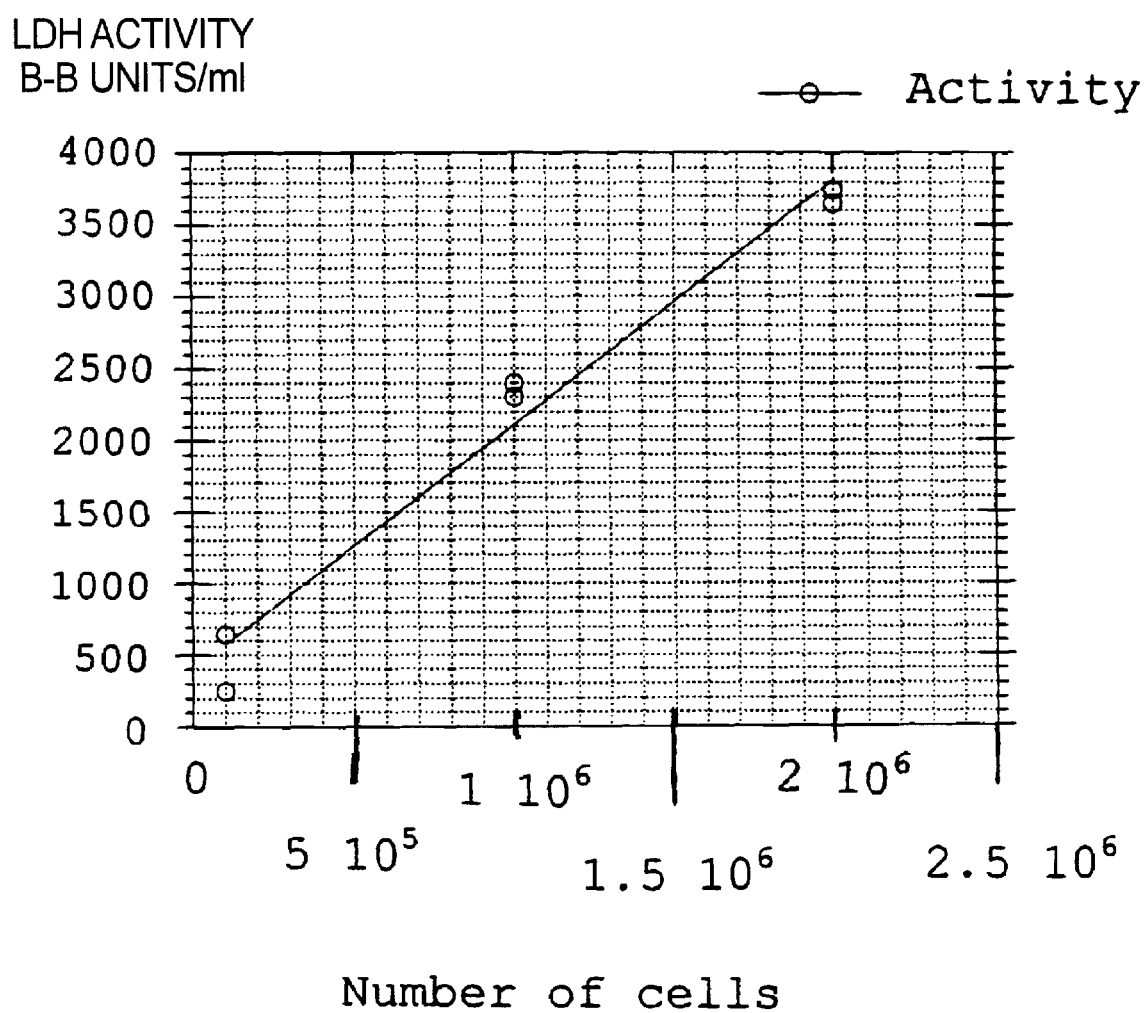
FIG. 4 illustrates the control of LDH activity in B—B units/ml, from dead human monocytes.

FIGS. 1A and 1B illustrate the biocompatibility of the piezomaterials according to the invention by means of the lactate dehydrogenase (LDH) activity as [B—B units/ml] in the culture medium after 23 and 46 h cultivation of 1×10$^6$ human monocytes, on a ceramic surface (Ceram), titanium (Ti) and on tissue culture polystyrene (Ps). The cells were from two separate blood donors, the results being respectively indicated as exp. 1 (FIG. 1A and exp. 2 (FIG. 1B). The values in the diagram are mean values, the standard error mean (SEM) also being indicated. FIG. 2 shows the LDH activity as μkatal/1, in the culture medium after 23 and 46 h cultivation of 1×10$^6$ human monocytes, on a ceramic surface, on titanium and on tissue culture polystyrene. Again cells from two separate blood donors were used, the results being respectively indicated as exp. 1 exp. 2 (FIG. 2b). Normal levels in human serum are 8 μkatal/1. The values are mean values±SEM. FIGS. 3A and 3B show the LDH activity as [B—B units/ml), normalized by total amount of DNA in wells after 46 h cultivation of 1×10$^6$ human monocytes on a ceramic surface, titanium and on tissue culture polystyrene. Cells from two separate blood donors, the results being respectively indicated as exp. 1 (FIG. 3A) and exp. 2 (FIG. 3B). The values are mean values±SEM. FIG. 4 illustrates the control of total LDH activity as [B—B units/ml), from dead human monocytes by adding 2% Triton X100 to 1×10$^5$, 1×10$^6$ and 2×10$^6$ human monocytes. The LDH activity between 500 and 700 corresponds approximately to 0.5–1.5×10$^5$ dead cells.

As is evident from these diagrams, the ceramic material according to the invention has a biocompatibility that closely follows that of titanium. In view of the fact that titanium has proved to be one of the most biocompatible materials and in view of the doubtful biocompatibility of known polarizable ceramic ferroelectrics, this is very unexpected in a ceramic ferroelectric.

Although the test relates to Na$_{0.5}$K$_{0.5}$NbO$_3$, it obviously also is valid for niobates with other proportions of Na and K.

The material may for instance be used as a layer covering the conducting tip on an electrode for sensing/stimulating cardiac tissue, this layer being in direct contact with conducting liquid in blood/tissue. The conducting tip then will function as one plate of a capacitor and the liquid as the other plate, the piezo material being the dielectric. The layer thus will react to a charge applied onto the plates by generating a mechanical force. The layer will also generate a charge if a mechanical force is applied. By these means the cardiac tissue may be stimulated mechanically as well as electrically when a stimulating pulse is applied to the electrode. Conversely a pressure variation in the blood or a myocardial contraction will generate a charge that can be utilized for sensing purposes.

Figure 5A:
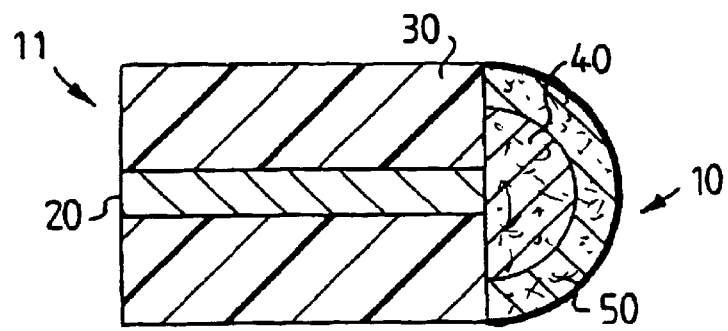
FIGS. 5A and 5B respectively show two embodiments of a tip electrode in accordance with the invention, for electrically and mechanically stimulating tissue and detecting an evoked response.
Figure 5B:
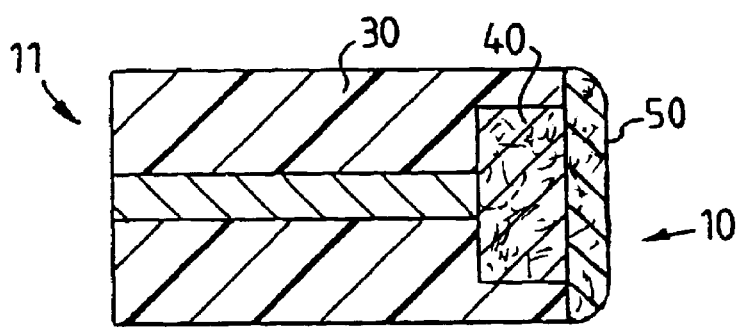

With reference to FIGS. 5A and 5B, there is shown an electrode 10 for a heart pacemaker. The electrode 10 has a conductor 20 enclosed by an insulator 30, e.g. silicon rubber. The conductor 20 is at one end in contact with an electrically conductive core 40, which is covered with a piezoelectric material 50 formed of Na$_{0.5}$K$_{0.5}$NbO$_3$. In order to obtain a high capacitance, usually of the order 10–100 nF, the layer of piezoelectric material is very thin (0.1–5 μm). The conductive core 40 and the piezoelectric layer 50, i.e. the piezoelectric electrode, form the tip of the electrode lead 11. FIGS. 5A and 5B show a hemispherical and a planar embodiment of the tip respectively, the planar embodiment being more sensitive to how it is placed with respect to the myocardial tissue. In a preferred embodiment the conductor 20 is made of the commonly used alloy MP3S and the conductive core 40 of e.g. graphite, titanium, platinum or iridium. The size of the electrode is about the same as for standard electrodes and may for instance vary between 1–10 mm$^2$.

Figure 5C:
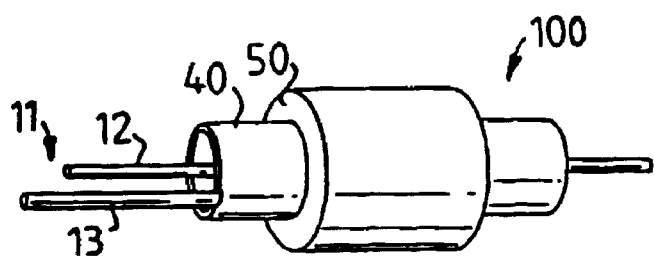
FIG. 5C shows an embodiment of a ring electrode in accordance with the invention, for electrically and mechanically stimulating tissue, and detecting an evoked response.
Figure 5D:
FIG. 5D schematically illustrates an electrode lead in accordance with the embodiment of the invention.

According to another embodiment of the electrode, FIGS. 5C and 5D show a coaxial stimulating and sensing piezoelectric electrode 40,50. The coaxial piezoelectric electrode 40,50 is positioned about 1 to 15 cm behind the tip having an endocardial stimulation electrode 200. This embodiment may e.g. be used in a single lead DDD pacemaker system as disclosed in U.S. Pat. No. 5,476,499. The tip is thereby screwed into the atrial myocardium and a loop descends into the ventricle and makes contact with the ventricular wall. The design of the lead 11 is such that the ring 100 of the lead 11 is found in the contact area and the ring 10 contains the coaxial piezoelectric electrode 40,50. The lead 11 must have two conductors in this case. One conductor 12 is connected to the tip and atrial part of the DDD pacemaker. The other conductor 13 is connected to the piezoelectric electrode 40,50 and the ventricular circuits of the pacemaker.

FIG. 5E shows a schematic equivalent circuit 45 of the above electrodes, whereby the piezoelectric electrode 40,50 comprises a voltage source $V_p$ and a capacitor $C_p$. The electrode 10 is further characterized by the tip surface 50. The conductor 13, 20 electrically connects the electrode to the electronics of the pacemaker.

A stimulation pulse delivered to the electrode 10 and thus to the piezo electrode 45, will change the thickness of the piezoelectric material during the pulse and two pressure waves will be emitted therefrom, there being one pressure wave for each slope of the stimulation wave. The capacitor $C_p$ of the piezoelectric electrode 40,50 transmits the electrical stimulation pulse to the heart cells.

To avoid charging of the piezoelectric material, the material can be doped or contaminated with a conducting material such as carbon. It is conceivable to have different time constants for the charging. A short time constant, for instance 10–100 ms, entails that the charge has been dissipated before the mechanical response arrives. In this case, only fast events can be monitored/detected (>20 Hz). An alternative is to provide a slow discharge during for instance 1–10 seconds, which prevents a cumulative charge, but which permits a relatively low cut-off frequency fg. If the total resistance against leaking over the piezo-material is termed R and the total capacitance is termed C, the following examples can be given:

EXAMPLE 1

Fast Tip
C=10 nF, R=500 kohm⇒τ=RC=5 ms⇒fg=32 Hz

EXAMPLE 2

Slow Tip
C=100 nF, R=5 Mohm⇒τ=RC=0.5 s⇒fg=0.32 Hz

One way of using the above electrode is described below.

FIG. 6 shows a pulse diagram of a detector input signal generated by the electrode in accordance with an embodiment of the invention and comprising the stimulation pulse, the electrical evoked response A and the electrical signal B corresponding to the mechanical evoked response. Consequently, successful heart stimulation will be sensed as two electrical signals by a detector in a pacer. First the muscle cells close to the electrode will generate an electrical signal A immediately after the stimulation pulse related to the triggered ion transport. Then the global heart muscle contraction will exert a mechanical pressure on the piezo electrode 45 which generates the second electrical signal B. The electrical signal B arrives within a time window C after a certain time D of the electrical signal A. The time interval D depends on the location of the electrode and on the activity of the autonomic nervous system. However, the time interval D is substantially constant for each individual. The time interval D is approximately 5 to 100 ms if the electrode is located in the ventricle. Furthermore, the electrical signal B appears in a relatively narrow time window C, which is approximately 50 ms if the electrode is located in the ventricle.

By letting a control unit, e.g. a microprocessor, comprise means for analyzing the detected electrical signals A and B and how they relate to each other and to the stimulation pulse, information regarding the condition of the heart can be obtained. This information therefore can be used as a diagnostic tool for analyzing the condition of the heart.

The control unit may obtain information from the dual sensing detector for analyzing the evoked response signals. It is e.g. often difficult to handle fusion beats in pacemakers comprising an autocapture function. A fusion beat is a cardiac depolarization (atrial or ventricular) resulting from two foci. In pacing it typically refers to the ECG waveform which results when an intrinsic depolarization and a pacemaker output pulse occur simultaneously and both contribute to the electrical activation of that chamber. Another difficulty when analyzing evoked response signals is related to the declining electrode polarization after the stimulation pulse. If the polarization artefact is large, compared to the electrical signal generated by the heart, the control unit may interpret the polarization as a capture. A capture is at hand when the stimulation results in a heart contraction.

Using this electrode, a new possibility for the control unit to verify capture has been created. If the electrical signal B does not fall within the time interval C, the heart contraction is probably not related to the stimulation pulse. If the electrical signal B arrives before the time window C, a fusion beat is present, or the QRS detector sensitivity is set too low, so that the pacemaker does not inhibit the pacing pulse. If the electrical signal B arrives after the time window C, there is a loss of capture followed by a spontaneously released heart beat.

If only the electrical signal A is present, the detector either senses the polarization artefact due to the sensitivity being too high and should be adjusted, i.e. evoked response oversensing, or the patient has a beat with electromechanical dissociation.

By analyzing the morphology, i.e. duration and amplitude, of the electric signal B, information regarding the heart contractility can be obtained. For patients with coronary artery disease during angina pectoris, the contractile behavior is changed. With the electrode according to the invention it is possible for the pacemaker to detect this adverse situation and start therapy. The pacing rate should be reduced until the attack is over. This function is especially important for physiologically rate controlled pacemakers such as the ones being controlled by the venous oxygen contents.

Certain patients have a prolonged or varying time between the atrial stimulation and the atrial evoked electrical response A. By letting the control unit start the A-V timer in a two chamber pacing system after the detection of the electrical signal B corresponding to the mechanical evoked response, instead of after the evoked electrical response, these patients will obtain a more stable heart function. The A-V timer is the timer keeping track of the time elapsed between the atrial electrical response A and the ventricular stimulation V.

There are times when the heart in response to a stimulation pulse emits an electrical signal, but does not actually contract (electromechanical dissociation). However, the pacemaker still would detect and interpret the electrical signal as an evoked response. The fact that in fact there is no evoked response thus can be determined by means of the electrode according to the invention.

Since the electrode according to the invention registers both electrical and mechanical evoked response, it can distinguish e.g. hemodynamically stable tachycardias at exercise from a pathological situation. Consequently, the electrode according to the invention is suitable for therapy when using an implantable cardiac defibrillator.

In an alternative embodiment of the above electrode, the stimulation pulse generator may generate a stimulation pulse that is chopped with a high frequency of e.g. 10 to 100 kHz in order to influence the stimulation threshold. Due to the chopped stimulation pulse, the piezo sensor generates a series of pressure waves.

The piezoelectric electrode 10 may be used together with a defibrillation electrode, either as two separated electrodes, i.e. two leads, or in combination on a single lead, whereby the piezoelectric electrode is placed at the tip of the lead and the intravascular defibrillation electrode is placed behind the piezo electrode 10.

Thus an electrode for electrically and mechanically stimulating and detecting evoked response is provided.

The electrode may for instance be used for sensing purposes only (e.g. pressure and/or contraction) or for stimulating purposes only.

Those skilled in the art will appreciate that the present invention can be practiced in other ways than by means of the described embodiments, which are presented for purposes of illustration.

The implant material may for instance be used in all applications in the body utilizing piezoelectric effects, such as vibrating implanted medication dispensing orifices in order to keep the orifices from clotting.

What is claimed is:

1. A medical implant comprising:

an element adapted for implantation in a living subject, said element having at least one part adapted for contact with tissue of said living subject; and said at least one part composed of piezoelectric material adapted for contact with tissue of said living subject; and said piezoelectric material comprising $Na_xK_yNbO_3$, wherein $0 \leq x \leq 0.8$, $0.2 \leq y \leq 1$, and $x+y=1$.

2. A medical implant as claimed in claim 1 wherein $0.2 \leq x \leq 0.8$ and $0.2 \leq y \leq 0.8$.

3. A medical implant as claimed in claim 1 wherein $0.4 \leq x \leq 0.6$ and $0.4 \leq y \leq 0.6$.

4. A medical implant as claimed in claim 1 wherein $x=y=0.5$.

5. A medical implant as claimed in claim 1 wherein said piezoelectric material has a relative density exceeding 97%.

6. A medical implant as claimed in claim 1 wherein said piezoelectric material has a pore size of less than 4 μm.

7. A medical implant as claimed in claim 1 wherein said piezoelectric material has a grain size of less than 4 μm.

8. A medical implant as claimed in claim 1 wherein said piezoelectric material has a piezoelectric constant $d_{33}$ exceeding 100 pCN$^-$.

9. A medical implant as claimed in claim 1 wherein said element is an electrode lead, and wherein said part composed of piezoelectric material is a piezoelectric electrode carried by said electrode lead for electrically stimulating said tissue.

10. A medical implant as claimed in claim 9 further comprising a tissue stimulator connected to said electrode lead.

11. A medical implant as claimed in claim 1 wherein said element is an electrode lead, and wherein said part composed of piezoelectric material is a sensor for sensing physiological variables in said tissue.

12. A medical implant as claimed in claim 11 further comprising a tissue stimulator connected to said electrode lead.

13. A medical implant as claimed in claim 1 wherein said element is an electrode lead, and wherein said part composed of piezoelectric material is a piezoelectric electrode for participating in stimulation of said tissue and sensing of physiological variables in said tissue.

14. A medical implant as claimed in claim 13 further comprising a tissue stimulator connected to said electrode lead.

* * * * *